United States Patent
Lin et al.

(10) Patent No.: US 9,468,608 B2
(45) Date of Patent: Oct. 18, 2016

(54) PREPARATION METHOD OF RADIATION SENSITIVE COPOLYMER CARRIER FOR COATING RADIATED NANOPARTICLES AND CHEMOTHERAPY DRUGS

(71) Applicants: Wuu-Jyh Lin, Taoyuan County (TW); Ting-Shien Duh, Taoyuan County (TW); Wei-Ming Li, Taoyuan County (TW); Ming-Hsin Li, Taoyuan County (TW)

(72) Inventors: Wuu-Jyh Lin, Taoyuan County (TW); Ting-Shien Duh, Taoyuan County (TW); Wei-Ming Li, Taoyuan County (TW); Ming-Hsin Li, Taoyuan County (TW)

(73) Assignee: INSTITUTE OF NUCLEAR ENERGY RESEARCH, Taoyuan (TW)

( * ) Notice: Subject to any disclaimer, the term of this patent is extended or adjusted under 35 U.S.C. 154(b) by 392 days.

(21) Appl. No.: 14/522,583

(22) Filed: Oct. 24, 2014

(65) Prior Publication Data
US 2016/0113884 A1     Apr. 28, 2016

(51) Int. Cl.
*A61K 9/51* (2006.01)
*A61K 31/704* (2006.01)

(52) U.S. Cl.
CPC .......... *A61K 9/5146* (2013.01); *A61K 9/5192* (2013.01); *A61K 31/704* (2013.01)

(58) Field of Classification Search
CPC . A61K 9/5146; A61K 31/704; A61K 9/5192

USPC ........................................................ 427/2.14
See application file for complete search history.

(56) References Cited

PUBLICATIONS

Ma et al. Radiation Sensitive Diselenide Block Co polymer Micellar Aggregates: Toward the Combination of Radiotherapy and Chemotherapy. American Chemical Society 2011 pp. 5874-5878.*
Krief et al. Synthesis of diselenides and selenides from elemental selenium. Tetrahedron Letters 43 (2002) pp. 3083-3086.*
Ma et al. Dual Redox Responsive Assemblies Formed from Diselenide Block Copolymers. Journels of Americal Chemical Society, 2010, 132. pp. 442-443.*
Yang et al. A modified method to prepare diselenides by the reaction of selenium with sodium borohydride. J. Chem Research,2002 pp. 160-161.*

* cited by examiner

*Primary Examiner* — Cachet Sellman

(57) ABSTRACT

The preparation method of radiation-sensitive copolymer carrier for coating radiated nanoparticles and/or chemotherapy drugs includes forming a nanosphere by diselenide block copolymers and DSPE-PEG-biomarkers to coat chemotherapy drugs and/or radiated nanoparticles that can be released from the opened nanosphere by protons penetrating tissue during proton therapy. The treatment effect of proton therapy is enhanced by two ways of using the radiated nanoparticles released from an opened nanosphere to produce nuclear fission with the protons for releasing electrons to destroy cancer cells of tumor and the chemotherapy drugs released from the opened nanosphere for distributing among tissue to kill the cancer cells of the tumor.

7 Claims, 1 Drawing Sheet

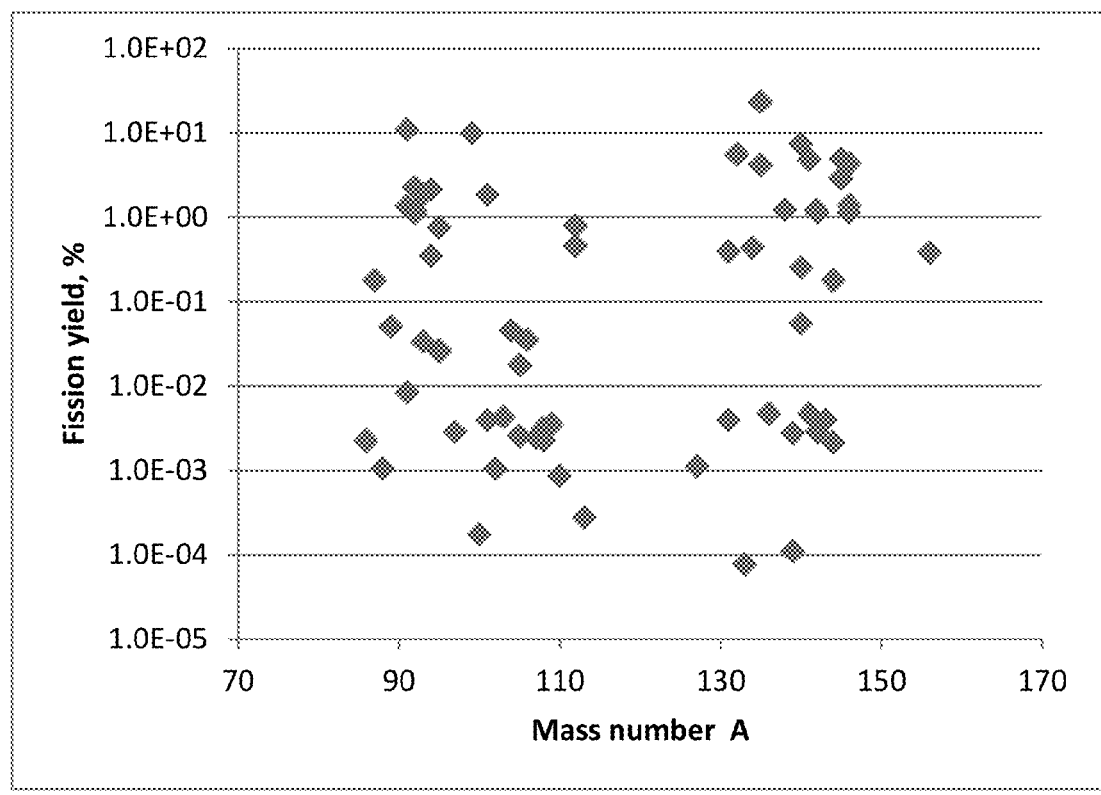

PREPARATION METHOD OF RADIATION SENSITIVE COPOLYMER CARRIER FOR COATING RADIATED NANOPARTICLES AND CHEMOTHERAPY DRUGS

BACKGROUND OF THE INVENTION

1. Field of the Invention

The field of the invention relates to a method of preparing the radiation-sensitive copolymer carrier for coating radiated nanoparticles and/or chemotherapy drugs used in proton therapy.

2. Description of the Related Art

Cancer, also known as malignant tumor, has been the first place of top ten causes of death for a long time; especially lung cancer and liver cancer are the most common types of cancer. Cancer occurs due to human cell diseases, and is treated in common clinical treatment of surgery, radiation, therapy, chemotherapy, and targeted therapy so far. Different treatment effects toward focus of infection of cancer vary from indications to assorted treatments.

The basic principle of radiation therapy is utilizing radioactivity to block the double helical chains in DNA (deoxyribonucleic acid) of cancer cell nucleus for the purpose of killing the cancer cells or inhibiting their growth. Traditional photon therapy that produces gamma radiation or X-radiation through human body, while the energy decaying exponentially relative to the increasing depth into tissue, many other normal tissue would be influenced by the radioactivity before cancer cells being destroyed. The feature of proton therapy is that the energy increasing with distance and slowing down at the range end, namely the location of targeted tumor, to release the maximum energy in an instant, forming a Bragg peak for providing effective treatment to cancer cells with high doses of chemotherapy drugs, and being almost no harm to healthy tissue. For the sake of proton therapy having the feature of spread-out Bragg peak (SOBP), the risk of damaging normal tissue during treatment can be reduced along with a minimum side effect relatively.

The physical characteristics of proton and X-radiation are different. X-radiation can treat tumor located in deep tissue for powerful penetration that accompanies defective effect of leaving high doses at forward tissue before reaching the tumor and damaging adjacent normal tissue with considerable residual doses after penetrating the tumor. Proton releases little energy during through tissue to reach the tumor, but discharges large energy in the tumor after reaching preferred depth of the tumor, the feature is called Bragg peak, without leaving any energy on normal tissue after penetrating the tumor. Because a single Bragg peak is not wide enough, it is necessary to combine several Bragg peaks to expand it to tumor size for enhancing proton therapeutic effect. Proton therapy is currently the most advanced tumor radiation therapy technology in the world for little damage to normal cells around the focus of infection and less side effects relatively, and is expected to be universalized in the future.

Traditional radiation therapy utilizes X-radiation to position and treat tumor, but is unable to accurately control the position and the dose for the tumor to avoid normal tissue between body surface and the tumor from receiving the dose and being damaged. A therapeutic method with accurate positioning and dose is in demand for cancer treatment.

US patent publication No. 2007/0031337 A1 discloses a method of proton tomography utilizing good combination characteristic of gold nanoparticle with antibody to attract antigen in the cancer cells to achieve better treatment positioning and chemotherapy drug dose control. Utilizing proton computer tomography (PCT) system for cancer treatment can be expected to become a trend in the future. However, the cited reference, US patent publication No. 2007/0031337 A1, didn't disclose the preparation of a carrier that can be utilized for coating radiated nonoparticles and/or chemotherapy drugs.

SUMMARY OF THE INVENTION

The primary object of the present invention is to provide a preparation method of radiation-sensitive copolymer carrier for coating nanoparticles and/or chemotherapy drugs. The method includes utilizing polymer of diselenide and 3-aminopropylpoly (ethylene gylycol) to react with each other to obtain diselenide block copolymer as a nano pharmaceutical carrier having hydrophilicity and hydrophobicity for forming a nanosphere by self-assembling in emulsification.

1,2-Distearoyl-sn-Glycero-3-Phosphoethanolamine-PEG-biomarker (hereinafter referred to as DSPE-PEG-biomarker) is another polymer having hydrophilicity and hydrophobicity alike that can be added into the diselenide block copolymer during the emulsification. A stable structure of nanosphere is formed during self-assembling of the polymers, wherein hydrophobic groups of the polymers gathering is arranged by organic solvents, and hydrophilic groups of the polymers are exposed to external solution. The nanosphere produces water-repellent effect due to inner hydrophobicity after volatilization of the organic solvents.

The water-repellent effect makes the nanosphere be indestructible by blocking water molecules into the nanosphere and stable in solution with the outer hydrophilic groups of the nanosphere. The nanosphere produced by radiation-sensitive diselenide block copolymer of the present invention is stable in aqueous solution and preferable to be a potential nuclear pharmaceutical carrier for controlling collapse speed of the carrier by specific radiation.

BRIEF DESCRIPTION OF THE DRAWINGS

FIG. 1 is a chart of changes in distribution of radionuclide fission yield and mass number A.

DETAILED DESCRIPTION OF THE PREFERRED EMBODIMENTS

One preferred embodiment of preparation method of radiation-sensitive copolymer carrier for coating radiated nanoparticles and/or chemotherapy drugs of the present invention, comprising the steps of:

step 11: dissolving 2 g of 0.05 mole solid sodium hydroxide (NaOH) into 25 ml of water, and adding 3.95 g of 50 mole selenium powder and 100 mg of $C_{19}H_{42}BrN$ (cetyltrimethylammonium bromide, CTAB) to obtain a selenium solution;

step 12: dissolving 0.25 g of 6.6 mole sodium borohydride ($NaBH_4$) and 0.2 g of solid sodium hydroxide into 5 ml of water in ice bath to obtain a sodium borohydride solution, and instilling the selenium solution obtained in step 11 into the sodium borohydride solution to react under room temperature for about an hour, then reacting at about 90° C. for about half an hour to complete reaction and to obtain a red-brown alkaline solution of sodium selenide ($Na_2Se_2$);

step 13: dissolving 2-Dodecen-1-yl-succinic anhydride into $(CH_2)_4O$ (Tetrahydrofuran, THF) and adding into the alkaline solution of Na₂Se₂ to react for about 12 hours, separating impurities by column chromatography and utilizing anhydrous Na₂SO₄ or MgSO₄ to remove water to obtain diselenide after high temperature drying;

step 14: dissolving the diselenide obtained in step 13 into tetrahydrofuran with polyethylene glycol polymer having amino group, and adding 1-Ethyl-3 (-3-dimethylaminopropyl) carbodiimide (EDC) or N-Hydroxysuccinimide (NHS) to react for about 12 hours, separating impurities by column chromatography to obtain diselenide block copolymer after high temperature drying.

The method of binding diselenide block copolymer with DSPE-PEG-biomarker to form a nanosphere as carrier for coating radiated nanoparticles and/or chemotherapy drug has three types which are described as follows, respectively.

1. The method of coating radiated nanoparticles comprises: dissolving 10 mg of diselenide block copolymer as the main ingredient of the carrier and 2 mg of DSPE-PEG-biomarker as stabilizer for forming a nanosphere structure of the carrier with 5 ml of ultrapure water; adding 1 ml of dichloromethane organic solvent having 4 mg of oil phase radiated nanoparticles dissolved, wherein the proportion of diselenide block copolymer, DSPE-PEG-biomarker, and oil phase radiated nanoparticles is 5:1:2; completing emulsification with sonication in ice bath; and heating to 60° C. to remove the dichloromethane organic solvent to obtain radiation-sensitive nanoparticles that carry radiated nanoparticles (RNPs-Radiation-Sensitive nanoparticles) in size of about 100 nanometers.

2. The method of coating chemotherapy drug comprises: dissolving 10 mg of diselenide block copolymer and 2 mg of DSPE-PEG-biomarker with 5 ml of ultrapure water; adding 1 ml of dichloromethane organic solvent having 4 mg of doxorubicine dissolved, wherein the proportion of diselenide block copolymer, DSPE-PEG-biomarker, and doxorubicin is 5:1:2; completing emulsification with sonication in ice bath; and heating to 60° C. to remove the dichloromethane organic solvent to obtain radiation-sensitive nanoparticles carrying doxorubicin (DOX-Radiation-Sensitive nanoparticles) in size of about 100 nanometers.

3. The method of coating radiated nanoparticles and chemotherapy drug comprises: dissolving 10 mg of diselenide block copolymer and 2 mg of DSPE-PEG-biomarker with 5 ml of ultrapure water; adding 1 ml of dichloromethane organic solvent having 2 mg of oil phase radiated nanoparticles and 2 mg of doxorubicine dissolved, wherein the proportion of diselenide block copolymer, DSPE-PEG-biomarker, oil phase radiated nanoparticles, and doxorubicin is 5:1:1:1; completing emulsification with sonication in ice bath; and heating to 60° C. to remove the dichloromethane organic solvent to obtain radiation-sensitive nanoparticles carrying radiated nanoparticles and doxorubicin (RNPs/DOX-Radiation-Sensitive nanoparticles) in size of about 120 nanometers.

Proton therapy that utilizes chemotherapy drugs made by the radiation-sensitive copolymer carrier of the present invention has decreasing proton energy in proportion with penetrated depth while the high-energy protons are hitting into the human body. The protons energy may decrease to one-third or one-fourth of primary energy while the protons are reaching to the cancer according to the penetration depth and incident energy of the protons. The incident protons having energy at 10-1000 MeV will cause fission reaction of uranium-238 with certain probability while impacting the uranium-238 distributed on the cancer. FIG. 1 shows the fission reaction while protons are impacting uranium-238, wherein the fission yields varies with the mass distribution. These fission products are usually unstable nuclides and subject to continuing decay reactions.

Table 1 lists nuclide names of fission products having higher incidence energy and related data of decay reaction that occurred after nuclear fission following proton (the incident energy of high energy proton is 10~250 MeV) striking uranium-238. These fission products will release high energy electrons during decaying process that is to be applied to destroy cancer cells of tumor for enhancing treatment effect after patients finishing their proton therapy.

TABLE 1

| | yield, % | half life | decay mode | decay energy (keV) (intensity %) |
|---|---|---|---|---|
| ¹³⁵Te | 23.0 | 19.0 s | % Beta- = 100 | Beta-: 5960 (50%), 5356 (25%), 5090 (%16) |
| ⁹¹Sr | 10.8 | 9.63 h | % Beta- = 100 | Beta-: 2707 (29%), 1402 (25%), 1127 (%34.7) |
| ⁹⁹Mo | 9.9 | 65.94 h | % Beta- = 100 | Beta-: 1214 (82.4%), 437 (16.4%) |
| ¹⁴⁰La | 7.3 | 1.6781 d | % Beta- = 100 | Beta-: 1679 (19.2%), 1246 (5.7%), 1240 (%10.9) |
| ¹³²Te | 5.5 | 3.204 d | % Beta- = 100 | Beta-: 215 (100%) |
| ¹⁴⁵La | 4.8 | 24.8 s | % Beta- = 100 | Beta-: 4110 (15%), 4040 (19%), 3992 (%15) |
| ¹⁴¹Ba | 4.8 | 18.27 m | % Beta- = 100 | Beta-: 3023 (7%), 2746 (18%), 2565 (%25) |
| ¹⁴⁶La | 4.3 | 6.27 s | % Beta- = 100 | Beta-: 6530 (18%), 6272 (28%), 5603 (%5.5) |
| ¹³⁵I | 4.2 | 6.57 h | % Beta- = 100 | Beta-: 1388 (23.8%), 1083 (8%), 970 (%21.9) |

It is obvious from the content mentioned above that the preparation method of radiation-sensitive copolymer carrier for coating radiated nanoparticles and/or chemotherapy drugs of the present invention indeed improves the effect of chemotherapy drugs and the accuracy of drug positioning for the treatment.

The foregoing invention has been described in detail by way of illustration and example for purposes of clarity and understanding. It will be apparent to those of ordinary skill in the art that variations, changes, modifications and alterations may be applied to the compositions and/or methods described herein without departing from the true spirit, concept and scope of the invention.

What is claimed is:

1. A preparation method of radiation-sensitive copolymer carrier for coating radiated nanoparticles and/or chemotherapy drugs, comprising:
dissolving solid sodium hydroxide into water and adding selenium powder and cetyltrimethylammonium bromide to obtain a selenium solution;
dissolving sodium borohydride and another solid sodium hydroxide into water in ice bath to obtain a sodium borohydride solution, and instilling the selenium solution into the sodium borohydride solution for reacting under room temperature for about an hour, then reacting at about 90° C. for about half an hour to complete the reaction and to obtain a alkaline solution of sodium selenide;
dissolving 2-Dodecen-1-yl-succinic anhydride into tetrahydrofuran and adding into the alkaline solution of sodium selenide to react for about 12 hours, separating impurities by column chromatography and utilizing anhydrous Na₂SO₄ or MgSO₄ to remove water to obtain diselenide after high temperature drying;
dissolving the diselenide into tetrahydrofuran with polyethylene glycol polymer having amino group, and adding 1-Ethyl-3(-3-dimethylaminopropyl)carbodiimide or N-Hydroxysuccinimide to react for about 12 hours, separating impurities by column chromatography to obtain diselenide block copolymer after high temperature drying.

2. The method of claim 1, wherein the diselenide block copolymer is used for coating radiated nanoparticles comprises: dissolving diselenide block copolymer and DSPE-PEG-biomarker with ultrapure water; adding dichloromethane organic solvent having oil phase radiated nanoparticles dissolved, wherein the proportion of the diselenide block copolymer, the DSPE-PEG-biomarker, and the oil phase radiated nanoparticles is 5:1:2; completing emulsification with sonication in ice bath; and heating to 60° C. to remove the dichloromethane organic solvent to obtain radiation-sensitive nanoparticles carrying the radiated nanoparticles (RNPs-Radiation-Sensitive nanoparticles).

3. The method of claim 1, wherein the diselenide block copolymer is used for coating chemotherapy drugs comprises: dissolving diselenide block copolymer and DSPE-PEG-biomarker with ultrapure water; adding dichloromethane organic solvent having doxorubicine dissolved, wherein the proportion of diselenide block copolymer, the DSPE-PEG-biomarker, and the doxorubicin is 5:1:2; completing emulsification with sonication in ice bath; and heating to 60° C. to remove the dichloromethane organic solvent to obtain radiation-sensitive nanoparticles carrying the doxorubicin (DOX-Radiation-Sensitive nanoparticles).

4. The method of claim 1, wherein the diselenide block copolymer is used for coating radiated nanoparticles and chemotherapy drugs comprises: dissolving diselenide block copolymer and DSPE-PEG-biomarker into ultrapure water; adding dichloromethane organic solvent having oil phase radiated nanoparticles and doxorubicine dissolved, wherein the proportion of the diselenide block copolymer, the DSPE-PEG-biomarker, the oil phase radiated nanoparticles, and the doxorubicin is 5:1:1:1; completing emulsification with sonication in ice bath; and heating to 60° C. to remove the dichloromethane organic solvent to obtain radiation-sensitive nanoparticles carrying the radiated nanoparticles and the doxorubicin (RNPs/DOX-Radiation-Sensitive nanoparticles).

5. The method of claim 2, wherein the RNPs-Radiation-Sensitive nanoparticle is in size of about 100 nanometers, and the radiated nanoparticle is uranium-238.

6. The method of claim 3, wherein the DOX-Radiation-Sensitive nanoparticle is in size of about 100 nanometers, and the pharmaceutical is doxorubicin.

7. The method of claim 4, wherein the RNPs/DOX-Radiation-Sensitive nanoparticle is in size of about 120 nanometers, the radiated nanoparticle is uranium-238, and the pharmaceutical is doxorubicin.

* * * * *